United States Patent

Barkóczy et al.

[11] Patent Number: 5,175,163
[45] Date of Patent: Dec. 29, 1992

[54] TRIAZOLYL THIOAMIDE DERIVATES

[75] Inventors: Jozsef Barkóczy; Jozsef Reiter; László Pongó; Lujza Petöcz; Márton Fekete; Frigyes Görgényi; Gábor Gigler; István Gacsályi; István Gyertyán, all of Budapest, Hungary

[73] Assignee: Egis Gyógyszergyar, Budapest, Hungary

[21] Appl. No.: 617,126

[22] Filed: Nov. 21, 1990

[30] Foreign Application Priority Data

Nov. 24, 1989 [HU] Hungary .............................. 6163/89

[51] Int. Cl.⁵ ................ A61K 31/495; A61K 31/445; C07D 401/14; C07D 403/04
[52] U.S. Cl. .................................. 514/255; 544/364; 544/366
[58] Field of Search ................ 544/364, 366; 514/255

[56] References Cited

U.S. PATENT DOCUMENTS 2,352,944   7/1944   D'Alello ........................... 260/308
4,421,753  12/1983   Tomcufcik et al. ............... 544/366

FOREIGN PATENT DOCUMENTS 949170   2/1964   United Kingdom .

OTHER PUBLICATIONS

T. Hirata et al., '5-Azapurines and the Structures of Sym-Triazole Intermediates', Journal of Heterocyclic Chemistry, Feb. 1972; Bd. 9, Nr. 1, Provoh US, pp. 99–106.

Reiter et al., "On Triazoles, XII, etc.", J. Heterocyclic Chem., 24, 1685–1695 (1987).

Primary Examiner—Patricia L. Morris
Attorney, Agent, or Firm—Beveridge, DeGrandi & Weilacher

[57] ABSTRACT

The invention relates to novel triazolyl thioamides of the general formula (I),

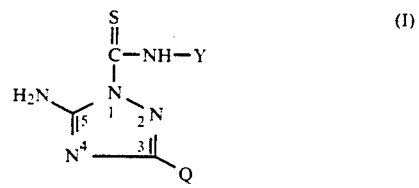

wherein
Q represents hydrogen or a heterocyclic group optionally bearing one or more $C_{1-4}$ alkyl substituent(s), or a group of the formula $SR^1$, wherein
  $R^1$ stands for straight or branched chained alkyl group comprising 1 to 6 carbon atom(s), or a group of the formula $NR^2R^3$, wherein
    $R^2$ and $R^3$ each represent hydrogen, straight or branched chained $C_{1-4}$ alkyl or $C_{2-6}$ alkenyl group,
Y denotes $C_{1-4}$ alkyl optionally bearing one or more hydroxyl or $C_{1-4}$ alkoxy substituent(s), phenyl-($C_{1-4}$ alkyl) optionally bearing on the phenyl ring one or more $C_{1-4}$ alkoxy group(s), or phenoxy-($C_{1-4}$ alkyl) optionally substituted on the phenyl ring by a $C_{1-4}$ alkyl bearing a heterocyclic group containing a nitrogen atom, and pharmaceutically acceptable acid addition salts thereof.

Furthermore the invention relates to a process for preparing these compounds.

The compounds according to the invention possess tranquillant, antidepressant, spacmolytic, antiinflammatory, analgesic and antiperistaltic effects.

6 Claims, No Drawings

TRIAZOLYL THIOAMIDE DERIVATES

This invention relates to new triazolyl thioamide derivatives, a process for the preparation thereof, pharmaceutical compositions comprising the same, to the use of the said triazolyl thioamide derivatives for the treatment of diseases and for the preparation of pharmaceutical compositions suitable for the treatment of diseases.

According to an aspect of the present invention there are provided new triazolyl thiomide derivatives of the general formula (I)

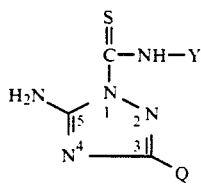

and pharmaceutically acceptable acid addition salts thereof, wherein

Q represents hydrogen or a heterocyclic group optionally bearing one or more $C_{1-4}$ alkyl substituent(s), or a group of the formula $SR^1$, wherein
  $R^1$ stands for straight or branched chained alkyl group comprising 1 to 6 carbon atom(s), or a group of the formula $NR^2R^3$, wherein
  $R^2$ and $R^3$ each represent hydrogen, straight or branched chained $C_{1-4}$ alkyl or $C_{2-6}$ alkenyl group,
Y denotes $C_{1-4}$ alkyl optionally bearing one or more hydroxyl or $C_{1-4}$ alkoxy substituent(s), phenyl-($C_{1-4}$ alkyl) optionally bearing on the phenyl ring one or more $C_{1-4}$ alkoxy group(s), or phenoxy-($C_{1-4}$ alkyl) optionally substituted on the phenyl ring by a $C_{1-4}$ alkyl bearing a heterocyclic group containing a nitrogen atom.

The invention encompasses all the isomers or tautomeric forms of the compounds of general formula (I).

The compounds according to the present invention posses tranquillant, antidepressant, spasmolytic, antiinflammatory, analgesic and antiperistaltic effects, furthermore they can be used as starting materials of other pharmaceutically active derivatives as well.

The term "heterocyclic group" used throughout the specification relates to 4 to 8 membered heterocyclic groups which can be formed from compounds comprising independently one or more nitrogen and/or oxygen atom(s) or a group which can be obtained by condensing the same compounds with each other or with benzene. Such groups may be aromatic or partially or completely saturated. As examples for such groups e.g. the piperidyl, morpholinyl, piperazinyl, furyl, imidazolyl, pyridyl, pyrimidinyl, pyrrolyl, pyrazolyl, pyridazinyl, isoxazolyl, pyrrolinyl, pyrrolidinyl, imidazolidinyl, imidazolinyl, pyrazolidinyl, pyrazolinyl, pyranyl or delta-3-piperidin-1-yl groups are mentioned.

The term "alkyl group" relates to straight or branched chained saturated aliphatic hydrocarbon groups having 1 to 4 or 1 to 6 carbon atom(s), e.g. methyl, ethyl, propyl, i-propyl, n-butyl, i-butyl, tert.butyl, pentyl, hexyl etc.

The term "alkoxy group" relates to alkyl ether groups comprising $C_{1-4}$ alkyl groups, e.g. methoxy, ethoxy, tert.butoxy etc.

As "$C_{2-6}$ alkenyl groups" straight or branched chained alkenyl groups are mentioned, e.g. vinyl, allyl, 2-methylallyl, 1-propenyl, 2-propenyl, 1-butenyl, 2-butenyl, 2-pentenyl, 2-hexenyl, etc.

Compounds of the general formula (I), wherein Q represents morpholino, di-($C_{1-6}$ alkyl)-amino or 4-methylpiperazinyl and Y stands for 3-[3-(-piperidinylmethyl)-phenoxy]-propyl or 2-phenylethyl optionally substituted by one or two $C_{1-4}$ alkoxy groups, and pharmaceutically acceptable acid addition salts thereof possess particularly valuable pharmaceutical properties.

Particularly preferred representatives of the compounds of the general formula (I) are the following derivatives: 1-[5-amino-3-(4-methylpiperazinyl)-1H-1,2,4-triazol-1-yl]-N-{3-[3-(1-piperidinylmethyl)-phenoxy]propyl}carbothioamide, 1-[5-amino-3-methylthio-1H-1,2,4-triazol-1-yl]-N-[2-(3,4-di-methoxy-phenyl)ethyl]carbothioamide, 1-(5-amino-3-morpholino-1H-1,2,4-triazol-1-yl)-N-{3-[3-(1-piperidinylmethyl)pnehoxy]propyl}carbothioamide, 1-[5-amino-3-dimethylamino-1H-1,2,4-triazol-1-yl]-N-{3-[3-(1-piperidinylmethyl)phenoxy]propyl}carbothioamide, and pharmaceutically acceptable acid addition salts thereof.

The compounds of the general formula (I) are organic bases, so they can be transformed into acid addition salts. The pharmaceutically acceptable acid addition salts of the compounds of the general formula (I) can be formed with inorganic or organic acids. As examples for the pharmaceutically acceptable acid addition salts the hydrohalides (such as hydrochlorides or hydrobromides), carbonates, sulfates, acetates, fumarates, maleates, citrates, ascorbinates and tartarates can be mentioned.

According to a further aspect of the present invention there is provided a process for the preparation of triazolyl thioamide derivatives of the general formula (I) and pharmaceutically acceptable acid addition salts thereof, which comprises reacting a triazolyl dithioester of the general formula (II),

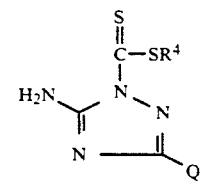

wherein Q is as stated above and $R^4$ represents $C_{1-4}$ alkyl or phenyl-($C_{1-4}$ alkyl) optionally substituted by a halogen atom,
with an amine derivative of the general formula (III),

wherein Y is as stated above, and, if desired, converting a compound of the general formula (I) thus obtained into a pharmaceutically acceptable acid addition salt thereof, or setting free a base of the general formula (I) from an acid addition salt thereof, or converting an acid addition salt of a base of the general formula (I) into another acid addition salt.

The reaction is preferably performed in a solvent inert toward the reactants. For this purpose preferably alcohols, (such as methanol, ethanol, propanol, i-propanol, n-butanol, i-butanol, tert.butanol), halogenated hydrocarbons (such as chloroform, dichloromethane, 1,2-dichloroethane, 1,1,2-trichloroethylene), dioxane or dimethyl sulfoxide can be used. The reaction is carried out at a temperature between 0° C. and 160° C., preferably between 20° C. and 120° C.

The compounds of the general formula (I) obtained in form of a base can be converted into acid addition salts by methods known per se. For this purpose the free base is reacted with the corresponding acid in an inert solvent.

The triazolyl esters of the general formula (II) used as starting materials are known compounds or can be produced on the analogy of the known compounds (U.S. Pat. specification No. 3,686,301; DD patent specification No. 105,897).

The amines of the general formula (III) are commercial products or can be produced as described in Houben-Weyl: Methoden der Organischen Chemie, Band XI/1, Georg Thieme Verlag, Stuttgart, 1957.

The compounds according to the present invention exhibit excellent biological activity and low toxicity. They possess tranquillant and/or antidepressant and spasmolytic effects which are accompanied in some cases by antiinflammatory, analgesic and antiperistaltic properties.

The activity of the compounds of the invention has been examined by the following tests.

1. Antagonism of tetrabenazine ptosis on mice Method

The tests were performed according to the method of Hoffmeister et. al. which was adapted to mice [Arzneim. Forschung 19, 846–858 (1969)]. Groups consisting of 10–20 mice each were treated perorally, with different doses of the compounds to be tested. The control group was treated only with the corresponding carrier. After 30 minutes tetrabenazine [3-isobutyl-9,10-dimethoxy-1,2,3,4,6,7-hexahydrobenzo[a]-quinolizine-2-one] was administered intraperitoneally at a dosage of 50 mg/kg. The number of animals having closed palpebral fissure was determined in each group after 30, 60, 90 and 120 minutes, resp.

Evaluation

The mean value of ptosis was calculated in each group, and the deviation from that of the control group (i.e. the inhibition) was expressed in percentage. From the data obtained the $ED_{50}$ value and the therapeutical index were determined for the novel compound tested as well as for amitryptiline. The results obtained are shown in Table I.

TABLE I

| Antagonism of tetrabenazine ptosis on mice | | | |
|---|---|---|---|
| Compound (Example No.) | $LD_{50}$ (mg/kg) | $ED_{50}$ (mg/kg) | Therapeutical index |
| 3 | >1000 | 11 | >90 |
| Amitryptiline | 225 | 12 | 18.7 |

The therapeutical index of the compound of the invention is several times higher than that of the amitryptiline widely used in the clinical practice with good results.

2. Antagonism of reserpine ptosis on mice Method

Groups consisting of 10 mice each were treated with 6 mg/kg of reserpine, subcutaneously, according to the method of Hoffmeister et. al. [Arzneim. Forschung 19, 846–858 (1969)] After 60 minutes the compounds tested were administered to the animals, while the animals of the control group were treated with the corresponding vehicle without the active agent. The animals with ptosis were counted 60 and 120 minutes after the administration of the compounds to be tested. Evaluation was carried out as given under the above test. The results obtained are shown in Table II.

TABLE II

| Antagonism of reserpine ptosis on mice | | | |
|---|---|---|---|
| Compound (Example No.) | $LD_{50}$ (mg/kg) | $ED_{50}$ (mg/kg) | Therapeutical index |
| 6 | >2000 | 20 | >100 |
| 1 | >2000 | 17 | >117 |
| Amitryptiline | 225 | 65 | 3.5 |

The compounds of the general formula (I) are superior to the reference compound concerning both the absolute dose and the therapeutical index.

3. Inhibition of pentetrazole spasm Method

The test was performed on white mice according to a modified method of Banziger and Hane [Arch. Int. Pharmacodyn. 167, 245 (1967)]. Each group of animals consisting of 6 mice was treated orally with the compound to be tested and the vehicle without active agent, respectively. One hour after the treatment a dosage of 125 mg/kg of pentetrazole was administered to each animal, intraperitoneally, and the tonic extensoric spasms of the hind limbs were recorded. The results are shown in Table III.

TABLE III

| Inhibition of pentetrazole spasm | | | |
|---|---|---|---|
| Compound (Example No.) | $LD_{50}$ (mg/kg) | $ED_{50}$ (mg/kg) | Therapeutical index |
| 1 | >2000 | 295 | >7 |
| 2 | >1000 | 64 | >15 |
| Trimethadion | 2050 | 490 | 4.3 |

From Table III it can be concluded that the compounds of the invention are superior to the reference compound concerning both the absolute dose and the therapeutical index.

4. Inhibition of nicotine spasm and lethality Method

The test was carried out according to the method of Stone. [Arch. Int. Pharmacodyn. 117, 419 (1958)]. The test compounds and the carrier, respectively, were administered orally; an hour later the animals received a 1.4 mg/kg i.v. dose of nicotine and the spasms and lethality were registered within an hour for the treated and control groups. The results are summarized in Table IV.

TABLE IV

| Inhibition of nicotine spasm and lethality | | | |
|---|---|---|---|
| Compound (Example No.) | $LD_{50}$ (mg/kg) | $ED_{50}$ (mg/kg) | Therapeutical index |
| 1 | >2000 | 68 | >29 |
| Trihexyphenidyl | 365 | 20 | 18.3 |

The therapeutical wideness of the test compound exceeds that of the trihexyphenidyl used as reference substance.

5. Hexobarbital nrcosis potentiating effect Method

The test was carried out on white mice with the aid of Kaergaard's method [Arch. Int. Pharmacodyn. 2, 170 (1967)]. Groups consisting of six mice were used for each dose. The test compound was administered orally and one hour after this treatment narcosis was induced by means of a 40 mg/kg i.v. dose of hexobarbital. The control group received carrier instead of the test compound.

Evaluation

Those mice were considered to have a positive reaction which show a narcosis time at least 2.5 times longer than that of the control group. The $ED_{50}$ values thus transformed were calculated. The results are summarized in Table V.

TABLE V

| Hexobarbital narcosis potentiating effect | | | |
|---|---|---|---|
| Compound (Example No.) | $LD_{50}$ (mg/kg) | $ED_{50}$ (mg/kg) | Therapeutical index |
| 1 | >2000 | 50 | >40 |
| 2 | >1000 | 110 | >9 |
| 5 | >1000 | 200 | >5 |
| Meprobamate | 1100 | 270 | 4.1 |

From the above Table it can be seen that the compounds according to the invention are superior to the reference substance considering both the absolute dose and the therapeutical index.

According to a further aspect of the present invention there are provided pharmaceutical compositions comprising as active ingredient at least one compound of the general formula (I) or a pharmaceutically acceptable acid addition salt thereof in admixture with suitable inert solid or liquid pharmaceutical carriers.

The pharmaceutical compositions of the present invention can be prepared by methods known per se by admixing the active ingredient with suitable inert solid or liquid carriers and bringing the mixture to galenic form.

The pharmaceutical compositions of the present invention may be suitable for oral (e.g. tablet, pill, coated pill, dragée, solid or soft gelatine capsule, solution, emulsion or suspension), parenteral (e.g. injection solution) or rectal (e.g. suppository) administration.

As carrier for the preparation of tablets, coated tablets, dragees and solid gelatine capsules e.g. lactose, corn starch, potatoe starch, talc, magnesium carbonate, magnesium stearate, calcium carbonate, stearic acid or the salts thereof, etc. can be used. As carrier for the soft gelatine capsules e.g. vegetable oils, fats, waxes or polyols of suitable consistency can be used. As carriers for the solutions and syrups e.g. water, polyols (polyethylene glycol), saccharose or glucose can be used. The injection solutions can comprise e.g. water, alcohols, polyols, glycerol or vegetable oils as carrier. The suppositories can be prepared with the aid of e.g. oils, waxes, fats or polyols of suitable consistency.

In addition, the pharmaceutical formulations may comprise auxiliaries usually applied in pharmaceutical industry, e.g. wetting, sweetening agents, aroma substances, salts causing the change of osmotic pressure, buffers, etc. The pharmaceutical formulations may further comprise other active ingredients, too.

The compounds of the general formula (I) can preferably be used in therapy orally in the form of tablets or capsules. Especially preferred are the capsules or tablets comprising about 250 mg of active ingredient.

The daily dose of the compounds of the general formula (I) can vary within wide ranges depending on several factors, e.g. on the activity of the active ingredient, the patient's condition and age, the severity of the disease, etc. The oral dose is generally 10 to 10,000 mg/day, preferably 50 to 1000 mg/day. It has to be stressed that these dose values are only of informative character and the administered dose must always be determined by the physician therapeutist.

According to a further aspect of the present invention there is provided the use of the compounds of the general formula (I) or pharmaceutically acceptable salts thereof for the preparation of pharmaceutical compositons having particularly tranquillant, antidepressant and/or spasmolytic effects.

According to a still further aspect of the present invention there is provided a method of tranquillant, anti-depressant and /or spasmolytic treatment, which comprises administering to the patient an effective amount of a compound of the general formula (I) or a pharmaceutically acceptable salt thereof.

The invention is further illustrated by the following Examples of non-limiting character.

EXAMPLE 1

1-(5-Amino-3-morpholino-1H-1,2,4-triazol-1-yl)-N-{3-[3-(1-piperidinylmethyl)phenoxyl]propyl}carbothioamide 2.59 g (0.01 mole) of methyl 1-(5-amino-3-morpholino-1H-1,2,4-triazol-1yl)carbodithioate are dissolved in 5 ml of dimethyl sulfoxide, and 2.48 g (0.01 mole) of 3-[3-(1-piperidinylmethyl)phenoxy]propylamine are added to the solution under water cooling. The reaction mixture is stirred at room temperature for 8 hours. Then it is poured onto water, the separated crystals are filtered off and recrystallized first from acetonitrile then from cyclohexane.

Yield: 2.89 (63%)

M.p.: 128° to 130° C.

EXAMPLE 2

1-[5-Amino-3-dimethylamino-1H-1,2,4-triazol-1-yl]-N-{3-[3-(1-piperidinylmethyl)phenoxy]propyl}carbothioamide 2.17 g (0.01 mole) of methyl 1-[5-amino-3-dimethylamino-1H-1,2,4-triazol-1-yl]carbodithioate are dissolved in 5 ml of dimethyl sulfoxide, and 2.48 g (0.01 mole) of 3-[3-(1-piperidinylmethyl)phenoxy]propylamine are added to the solution under water cooling. The reaction mixtue is stirred at room temperature for 8 hours. Then it is poured onto water, the separated crystals are filtered off and recrystallized from 2-propanol.

Yield: 2.83 g (68%)

M.p.: 104° to 106° C.

EXAMPLE 3

1-[5-Amino-3-(4-methylpiperazinyl)-1H-1,2,4-triazol-1-yl]-N-{3-[3-(1-piperidinylmethyl)phenoxy]propyl}carbothioamide 2.72 g (0.01 mole) of methyl 1-[5-amino-3-(4-methylpiperazinyl)-1H-1,2,4-triazol-1-yl-]carbodithioate are dissolved in 5ml of dimethyl sulfoxide, and 2.48 g (0.01 mole) of 3-[3-(1-piperidinylmethyl)phenoxy]propylamine are added to the solution under water cooling. The reaction mixture is stirred at room temperature for 8 hours. Then 1 ml of water is dropped to it, the mixture is stirred for 1 hour, thereafter 10 ml of n-hexane are dropwise added. The reaction mixture is further stirred for 1 hour, the separated crystals are filtered off and recrystallized from 2-propanol.

Yield: 2.83 g (68%)

M.p.: 92° to 93° C.

EXAMPLE 4

1-(5-Amino-3-piperidinyl-1H-1,2,4-triazol-1-yl)-N-{3-[3-(1-piperidinylmethyl)phenoxy]propyl}carbothioamide 2.57 g (0.01 mole) of methyl 1-(5-amino-3-piperidinyl-1H-1,2,4-triazol-1-yl)carbodithioate are dissolved in 5 ml of dimethyl sulfoxide, and 2.48 g (0.01 mole) of 3-[3-(1-piperidinylmethyl)phenoxy]propylamine are added to the solution under water cooling. The reaction mixture is stirred at room temperature for 8 hours. Then 1 ml of water is dropped to it, the mixture is stirred for 1 hour, thereafter 10 ml of n-hexane are dropwise added. The reaction mixture is further stirred for 1 hour, the separated crystals are filtered off and recrystallized from 2-propanol.

Yield: 3.74 g (82%)
M.p.: 107° to 108° C.

EXAMPLE 5

1-[5-Amino-3-diallylamino-1H-1,2,4-triazol-1-yl]-N-{3-[3-(1-piperidinylmethyl)phenoxy]propyl}carbothioamide 2.69 g (0.01 mole) of methyl 1-(5-amino-3-diallylamino-1H-1,2,4-triazol-1-yl)carbodithioate are dissolved in 5 ml of dimethyl sulfoxide, and 2.48 g (0.01 mole) of 3-[3-(1-piperidinylmethyl)phenoxy]propylamine are added to the solution under water cooling. The reaction mixture is stirred at room temperature for 8 hours. Then 1 ml of water is dropped to it, the mixture is stirred for 1 hour, thereafter 50 ml of n-hexane are dropwise added. The reaction mixture is further stirred for 1 hour, the separated crystals are filtered off and recrystallized from 2-propanol.

Yield: 3.65 g (78%)
M.p.: 94° to 96° C.

EXAMPLE 6

1-[5-Amino-3-methylthio-1H-1,2,4-triazol-1-yl]-N-[2-(3,4-dimethoxyphenyl)ethyl]carbothioamide 2.20 g (0.01 mole) of methyl 1-[5-amino-3-methylthio-1H-1,2,4-triazol-1-yl]carbodithioate are dissolved in 10 ml of dimethyl sulfoxide, and 1.81 g (0.01 mole) of 2-(3,4-dimethoxyphenyl)ethylamine are added to the solution under water cooling. The reaction mixture is stirred at room temperature for 8 hours. Then it is poured onto 15 ml of water, the separated crystals are filtered off and recrystallized from ethanol.

Yield: 2.44 g (69%)
M.p.: 135° to 137° C.

EXAMPLE 7

1-(5-Amino-3-morpholino-1H-1,2,4-triazol-1-yl)-N-[2-(3,4-dimethoxyphenyl)ethyl]carbothioamide 2.59 g (0.01 mole) of methyl 1-(5-amino-3-morpholino-1H-1,2,4-triazol-1-yl)carbodithioate are dissolved in 10 ml of dimethyl sulfoxide, and 1.81 g (0.01 mole) of 2-(3,4-dimethoxyphenyl)ethylamine are added to the solution under water cooling. The reaction mixture is stirred at room temperature for 8 hours. Then it is poured onto 15 ml of water, the separated crystals are filtered off and recrystallized from ethanol.

Yield: 2.66 g (84%)
M.p.: 142° to 143° C.

EXAMPLE 8

1-(5-Amino-3-morpholino-1H-1,2,4-triazol-1-yl)-N-(3-hidroxypropyl)carbothioamide 2.59 g (0.01 mole) of methyl 1-(5-amino-3-morpholino-1H-1,2,4-triazol-1-yl)carbodithioate are boiled in 25 ml of methanol, in the presence of 0.92 ml (0.12 mole) of 3-aminopropanol for 1 hour under stirring. The reaction mixture is then evaporated to dryness and the residue is recrystallized from acetonitrile.

Yield: 2.70 g (94%)
M.p.: 116° to 118° C.

EXAMPLE 9

1-(5-Amino-3-morpholino-1H-1,2,4-triazol-1-yl)-N-(3-hydroxypropyl)carbothioamide 2.59 g (0.01 mole) of methyl 1-(5-amino-3-morpholino-1H-1,2,4-triazol-1-yl) carbodithioate are boiled in 30 ml of dioxane, in the presence of 0.92 ml (0.12 mole) of 3-aminopropanol for 1 hour under stirring. The reaction mixture is then evaporated to dryness and the residue is recrystallized from methanol.

Yield: 2.48 g (84%)
M.p.: 116° to 118° C.

EXAMPLE 10

1-(5-Amino-3-morpholino-1H-1,2,4-triazol-1-yl)-N-(2-hydroxyethyl)carbothioamide 2.59 g (0.01 mole) of methyl 1-(5-amino-3-morpholino-1H-1,2,4-triazol-1-yl)carbodithioate are boiled in 25 ml of methanol, in the presence of 0.72 ml (0.12 mole) of 2-aminomethanol for 1 hour under stirring. The reaction mixture is then evaporated to dryness and the residue is recrystallized from water.

Yield: 2.47 g (91%)
M.p.: 146° to 148° C.

EXAMPLE 11

1-(5-Amino-3-morpholino-1H-1,2,4-triazol-1-yl)-N-(2-hydroxyethyl)carbothioamide 2.59 g (0.01 mole) of methyl 1-(5-amino-3-morpholino-1H-1,2,4-triazol-1-yl)carbodithioate are boiled in 30 ml of dioxane, in the presence of 0.72 ml (0.12 mole) of 2-aminoethanol for 1 hour under stirring. The reaction mixture is then evaporated to dryness and the residue is recrystallized from methanol.

Yield: 2.34 g (86%)
M.p.: 146° to 148° C.

EXAMPLE 12

1-[5-Amino-3-dimethylamino-1H-1,2,4-triazol-1-yl]-N-(2-hydroxyethyl)carbothioamide 2.17 g (0.01 mole) of methyl 1-[5-amino-3-dimethylamino-1H-1,2,4-triazol-1-yl]carbodithioate are boiled in 10 ml of ethanol, in the presence of 0.72 ml (0.12 mole) of 2-aminoethanol for 1 hour under stirring. The reaction mixture is then cooled, the separated crystals are filtered off and recrystallized from 2-propanol.

Yield: 1.89 g (82%)
M.p.: 148° to 150° C.

EXAMPLE 13

1-[5-Amino-3-(4-methylpiperazinyl)-1H-1,2,4-triazol-1-yl]-N-(2-hydroxyethyl)carbothioamide 2.72 g (0.01 mole) of methyl 1-[5-amino-3-(4-methylpiperazinyl)-1H-1,2,4-triazol-1-yl]carbodithioate are boiled in 10 ml of ethanol, in the presence of 0.72 ml (0.12 mole) of 2-aminoethanol for 1 hour under stirring. The reaction mixture is then cooled, the separated crystals are filtered off and recrystallized from 2-propanol.

Yield: 2.50 g (88%)
M.p.: 181° to 183° C.

EXAMPLE 14

1-(5-Amino-3-morpholino-1H-1,2,4-triazol-1-yl)-N-(2-hydroxyprop-1-yl)carbothioamide 2.59 g (0.01 mole) of methyl 1-(5-amino-3-morpholino-1H-1,2,4-triazol-1-yl)carbodithioate are boiled in 30 ml of dioxane, in the presence of 0.93 ml (0.12 mole) of 2-hydroxypropylamine for 2 hours under stirring. The reaction mixture is then evaporated to dryness and the residue is recrystallized from methanol.

Yield: 2.32 g (81%)
M.p.: 135° to 137° C.

EXAMPLE 15

1-(5-Amino-3-morpholino-1H-1,2,4-triazol-1-yl)-N-(2,2-dimethoxyethyl)carbothioamide 2.59 g (0.01 mole) of methyl 1-(5-amino-3-morpholino-1H-1,2,4-triazol-1-yl)carbodithioate are boiled in 30 ml of dioxane, in the presence of 1.3 ml (0.12 mole) of 2-aminoacetaldehyde dimethylacetale for 2 hours under stirring. The reaction mixture is then evaporated to dryness and the residue is recrystallized from ethanol.

Yield: 2.37 g (75%)
M.p.: 134° to 135° C.

EXAMPLE 16

1-(5-Amino-3-morpholino-1H-1,2,4-triazol-1-yl)-N-(2,2-dimethoxyethyl)carbothioamide 2.59 g (0.01 mole) of methyl 1-(5-amino-3-morpholino-1H-1,2,4-triazol-1-yl)carbodithioate are boiled in 20 ml of methanol, in the presence of 1.3 ml (0.12 mole) of 2-aminoacetaldehyde dimethylacetale for 4 hours under stirring. The reaction mixture is then cooled, the separated crystals are filtered off and recrystallized from ethanol.

Yield: 2.80 g (88%)
M.p.: 134° to 135° C.

EXAMPLE 17

1-(5-Amino-3-morpholino-1H-1,2,4-triazol-1-yl)-N-(2-methoxyethyl)carbothioamide 2.59 g (0.01 mole) of methyl 1-(5-amino-3-morpholino-1H-1,2,4-triazol-1-yl)carbodithioate are boiled in 30 ml of dioxane, in the presence of 1.03 ml (0.12 mole) of 2-methoxyethylamine for 4 hours under stirring. The reaction mixture is then evaporated to dryness and the residue is recrystallized from 2-propanol.

Yield: 2.06 g (72%)
M.p.: 103° to 105° C.

EXAMPLE 18

1-(5-Amino-3-methylthio-1H-1,2,4-triazol-1-yl)-N-(2-hydroxyehyl)carbothioamide 2.20 g (0.01 mole) of methyl 1-(5-amino-3-methylthio-1H-1,2,4-triazol-1-yl)carbodithioate are stirred in 12 ml of ethanol, in the presence of 0.72 ml (0.12 mole) of 2-aminoethanol at room temperature for 12 hours. The reaction mixture is then evaporated to dryness in vacuo and the residue is recrystallized from acetonitrile.

Yield: 0.68 g (29%)
M.p.: 131° to 132° C.

Example 19

1-(5-Amino-3-morpholino-1H-1,2,4-triazol-1-yl)-N-(2-hydroxybutan-1-yl)carbothioamide 2.59 g (0.01 mole) of methyl 1-(5-amino-3-morpholino-1H-1,2,4-triazol-1-yl)carbodithioate are stirred in 15 ml of dimethyl sulfoxide, in the presence of 0.95 ml (0.01 mole) of 2-aminobutanol at room temperature for 10 hours. Then 5 g of crushed ice and 10 ml of water are added to the reaction mixture, the separated product is filtered off and recrystallized from isopropanol.

Yield: 0.69 g (23%)
M.p.: 133° to 135° C.

EXAMPLE 20

1-(5-Amino-3-methylthio-1H-1,2,4-triazol-1-yl)-N-{3-[3-(1-piperidinylmethyl)phenoxy]propyl}carbothioamide 2.20 g (0.01 mole) of methyl 1-(5-amino-3-methylthio-1H-1,2,4-triazol-1-yl)carbodithioate are dissolved in 5 ml of dimethyl sulfoxide, then 2.48 g (0.01 mole) of 3-[3-(1-piperidinylmethyl)-phenoxy]propylamine are added to the reaction mixture under water cooling. It is stirred at room temperature for 5 hours. Thereafter a slight amount (about 1 ml) of water is dropped to it, the separated crystals are filtered off and recrystallized from ethanol.

Yield: 1.93 g (46%)
M.p.: 117° to 118° C.

EXAMPLE 21

1-(5-Amino-1H-1,2,4-triazol-1-yl)-N-{3-[3-(1-piperidinylmethyl)phenoxy]propyl}carbothioamide 1.74 g (0.01 mole) of methyl 1-(5-amino-1H-1,2,4-triazol-1-yl)carbodithioate are dissolved in 10 ml of dimethyl sulfoxide, then 2.48 g (0.01 mole) of 3-[3-(1-piperidinylmethyl)-phenoxy]propylamine are added to it. The reaction mixture is stirred at room temperature for 12 hours, then the separated crystals are filtered off and recrystallized from ethanol.

Yield: 1.57 g (42%)
M.p.: 102° to 105° C.

EXAMPLE 22

Tablets having the following composition are prepared by known methods of the pharmaceutical industry:

| Component | Amount, mg/tablet |
| --- | --- |
| 1-(5-Amino-3-morpholino-1H-1,2,4--triazol-1-yl)-N-{3-[3-(1-piperidinylmethyl)phenoxy]propyl}carbothioamide | 250 |
| Lactose | 61.8 |

| Component | Amount, mg/tablet |
|---|---|
| Potato starch | 43.2 |
| Polyvinylpyrrolidone | 22.5 |
| Stearic acid | 9.0 |
| Talc | 13.5 |
| Total weight: | 400 mg |

EXAMPLE 23

Ointments having the following composition are prepared by known methods of the pharmaceutical industry:

| Component | Amount, mg/tablet |
|---|---|
| 1-(5-Amino-3-morpholino-1H-1,2,4--triazol-1-yl)-N-{3-[3-(1-piperidinyl-methyl)phenoxy]propyl}carbothioamide | 500 |
| Unguentum hydrophilicum nonbonicum | 10.000 |

The active ingredient is in the outer phase of the ointment, in dissolved state.

EXAMPLE 24

Suppositories having the following composition are prepared by known methods of the pharmaceutical industry:

| Component | Amount, mg/tablet |
|---|---|
| 1-(5-Amino-3-morpholino-1H-1,2,4--triazol-1-yl)-N-{3-[3-(1-piperidinyl-methyl)phenoxy]propyl}carbothioamide | 100 |
| Lecithin | 48 |
| Cera alba | 96 |
| Cocoa butter | 1870 |
| Distilled water | 386 |
| Total weight: | 2500 mg |

EXAMPLE 25

Capsules having the following composition are prepared by known methods of the pharmaceutical industry:

| Component | Amount, mg/tablet |
|---|---|
| 1-(5-Amino-3-morpholino-1H-1,2,4,--triazol-1-yl)-N-{3-[3-(1-piperidinyl-methyl)phenoxy]propyl}carbothioamide | 50 |
| Lactose | 119 |
| Potato starch | 10 |
| Magnesium stearate | 1 |
| Total weight: | 180 mg |

What we claim is:

1. A triazolyl thioamide of the formula (I)

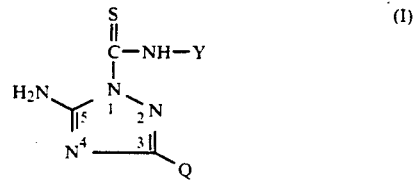

wherein

Q represents piperazinyl optionally bearing one or more $C_{1-4}$ alkyl substituent(s), and Y denotes $C_{1-4}$ alkyl optionally bearing one or more hydroxyl or $C_{1-4}$ alkoxy substituents, phenyl-($C_{1-4}$ alkyl) optionally bearing on the phenyl ring one or more $C_{1-4}$ alkoxy group(s), or phenoxy-($C_{1-4}$ alkyl) optionally substituted on the phenyl ring by a $C_{1-4}$ alkyl bearing a piperidinyl group, and pharmaceutically acceptable acid addition salts thereof.

2. The triazolyl thioamide as defined in claim 1 wherein Y is phenoxy-($C_{1-4}$ alkyl) optionally substituted on the phenyl ring by a $C_{1-4}$ alkyl bearing a piperidinyl group.

3. The triazolyl thioamide as defined in claim 2 wherein said piperazinyl is 4-methylpiperazinyl.

4. 1-[5-amino-3-(4-methylpiperazinyl)-1H-1,2,4-triazol-1-yl]-N-{3-[3-(1-piperidinylmethyl)phenoxy]-propyl}-carbothioamide.

5. Method of tranquillant, antidepressant and/or spasmolytic therapeutic treatment, which consists essentially of administering to a patient an effective amount of a triazolyl thioamide as defined in claim 1 or a pharmaceutically acceptable acid addition salt thereof, said effective amount being sufficient to impart the desired therapeutic effect.

6. A pharmaceutical composition having a tranquillant, anti-depressant and/or spasmolytic therapeutical effect consisting essentially of a triazolyl thioamide as defined in claim 1 or a pharmaceutically acceptable acid addition salt thereof in a dosage form sufficient to impart said therapeutic effect to a patient in need thereof, and an inert carrier therefor.

* * * * *